Figure 1:
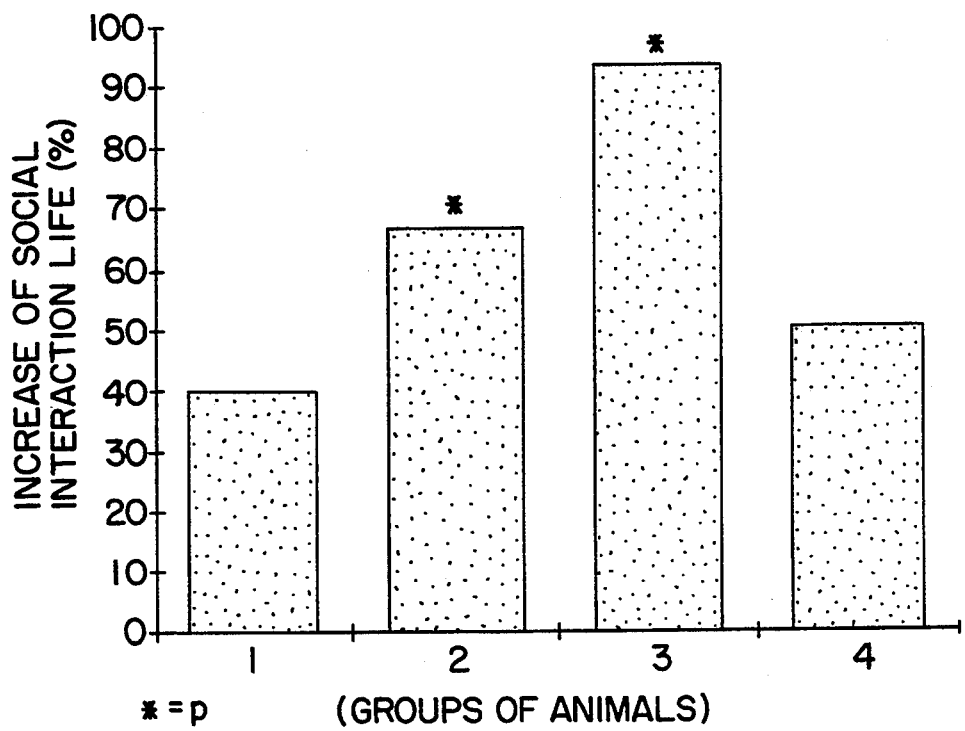

United States Patent [19]

Brufani et al.

[11] Patent Number: 5,401,853
[45] Date of Patent: Mar. 28, 1995

[54] THIADIAZOLE DERIVATIVES FOR THE TREATMENT OF DEPRESSIVE STATES

[75] Inventors: Mario Brufani, Castelgandolfo; Antonella Loche, Sanremo; Vincenzo Perlini, Matelica; Donato Pocar, Milan, all of Italy

[73] Assignee: Laboratorio Farmaceutico C.T. S.r.l., Sanremo, Italy

[21] Appl. No.: 89,747

[22] Filed: Jul. 9, 1993

[30] Foreign Application Priority Data

Jul. 14, 1992 [IT] Italy .................. MI92A1705

[51] Int. Cl.⁶ .............................. A01K 31/41
[52] U.S. Cl. .................... 514/363; 548/139; 548/141
[58] Field of Search ................ 548/139, 141, 363.1

[56] References Cited

U.S. PATENT DOCUMENTS 3,903,099 9/1975 Rathgeb .................. 548/141
4,639,526 1/1987 Metzger .................. 548/139

OTHER PUBLICATIONS

Dornow, Chem. Ber. 99, 72(1966).

Pharmaceutical Basis of Therapeutics, Goodman et al., Ital. Ed of 6th Amer. Ed., pp. 440–456 (1978).

Primary Examiner—Robert Gerstl
Attorney, Agent, or Firm—Hedman, Gibson & Costigan

[57] ABSTRACT

Thiadiazole derivatives of general formula (I)

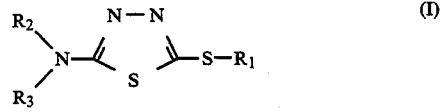

wherein $R_1$ is selected from the class consisting of: $C_1$–$C_{10}$ linear or branched alkyl, benzyl, optionally substituted at the aromatic ring with one or more groups selected on their turn from the class consisting of : $C_1$–$C_{20}$ linear or branched alkyl residues, nitro groups, halogen atoms, $C_1$–$C_{20}$ linear or branched alkoxy, hydroxy and $C_2$–$C_{20}$ linear or branched acyloxy groups, $R_2$ is selected from H, $C_2$–$C_{10}$ alkanoyl, cycloalkanoyl wherein this ring has from 3 to 10 carbon atoms, aroyl, and $R_3$ is selected from H and $C_1$–$C_{10}$ alkyl, for the treatment of depressive states and anxiety, a process for their preparation and relative pharmaceutical compositions containing them as the active ingredient.

4 Claims, 1 Drawing Sheet

THIADIAZOLE DERIVATIVES FOR THE TREATMENT OF DEPRESSIVE STATES

FIELD OF THE INVENTION

The present invention relates to thiadiazole derivatives, a process for their preparation and therapeutical compositions for the treatment of depressive states and anxiety containing them as the active ingredients.

PRIOR ART DISCLOSURE

As is well known depression is an affective disorder consisting of a mood descent, characterised by feeling of deep melancholy, pessimism, anxiety, self-pity, lack of ideas, organic symptoms (insomnia, anorexia, loss of enthusiasm and libido).

It can be treated for example with tricyclic antidepressants, with monoaminooxidase inhibition, with some antipsychotic drugs, with lithium carbonate and with the electroconvulsivant therapy (ECT or electroshock) (Goodman & Gilman "Pharmacological bases of the therapy" Italian edition to the sixth American Edition pp 440-456)

The treatment which in any case resulted the most effective is that encompassing the administration of tricyclic antidepressants, and particularly of imipramine.

This drug, like the other ones belonging to the class of tricyclic antidepressants, is very toxic (imipramine rat LD50: 90-110 mg/kg i.p., 400-490 mg/kg per OS.)

The majority of their toxic reactions involve their antimuscarinic effect and their toxicity at the cerebral level, but also the cardiac effects represent a serious problem, (Goodman & Gilman "Pharmacological bases of the therapy" Italian edition to the sixth American Edition pp 439-456).

An other tricyclic antidepressant drug: mianserine present a mouse LD50: 365-390 mg/kg per os, 31-32,5 mg/kg i.v..

THE PRESENT INVENTION

The Applicant has now unexpectedly found that thiadiazole derivatives of general formula (I)

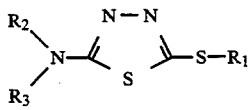

wherein $R_1$ is selected from the class consisting of: $C_1$-$C_{10}$ linear or branched alkyl, benzyl, optionally substituted at the aromatic ring with one or more groups selected on their turn from the class consisting of : $C_1$-$C_{20}$ linear or branched alkyl residues , nitro groups, halogen atoms. $C_1$-$C_{20}$ linear or branched alkoxy, hydroxy and $C_2$-$C_{20}$ linear or branched acyloxy groups, $R_2$ is selected from H, $C_2$-$C_{10}$alkanoyl, cycloalkanoyl wherein this ring has from 3 to 10 carbon atoms, aroyl, and $R_3$ is selected from H and $C_1$-$C_{10}$ alkyl, exhibit antidepressant activity, which is analogous or in some cases much higher than those respectively of imipramine and mianserine and contemporaneously they present a much lower toxicity (mouse LD50: equal to or higher than 600 mg/kg pep os) than that of the above known active ingredients. In addition the Applicant has also unexpectedly found that the derivatives of formula (I) are characterized by having anxiolythic activity.

Some of the derivatives comprised in general Formula (I) are already known.

In particular the thiadiazole derivatives wherein $R_1$ is benzyl, $R_2$ is $C_2$-$C_7$ acyl and $R_3$ is $C_1$-$C_6$ alkyl are described in GB 844.946, according to which they are used as intermediates for the preparation of thiadiazolsulphonamides which are on their turn utilized as antidiuretic agents, because of their ability to inhibit anhydrase enzyme.

The compounds of formula (I) wherein $R_2=R_3=H$ and $R_1=$benzyl, ethyl, methyl are already described in Beilstein 27,2, 783-785. The compounds of formula (I) wherein $R_2=R_3=H$ and $R_1$ is selected from:

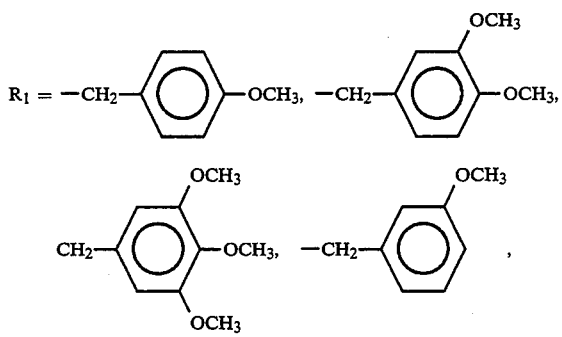

are disclosed in the Japanese Patent Application JP-62093284, as therapeutical agents for the treatment of hepatical diseases. The thiadiazole derivatives of formula (I) which resulted particularly useful as antidepressants according to the present invention are those belonging to one of the following classes: A) derivatives of formula (I) wherein $R_2=R_3=H$ and $R_1$ is methyl (B21), ethyl (B34), n-propyl (B32), isopropyl (B35), benzyl (B16), p-nitro-benzyl (B43), p-methoxy-benzyl (B51), p-Cl-benzyl (B57), p-methyl-benzyl (B58), 3, 4,5-trimethoxy-benzyl (B59), 3-methoxybenzyl (B63) p-hydroxy-benzyl (B92/2), m-mydroxybenzyl (B90/2), p-acetoxy-benzyl (B92/1) m-acetoxy-benzyl (B90/1), 3-methoxy-4-acetoxy-benzyl (B93), 3,4,5-trihydroxybenzyl, 3,4,5-triacetoxy-benzyl;

B) derivatives of formula (I) wherein $R_2=$—$COCH_3$, $R_3=H$, $R_1$ is selected from methyl (B37), n-propyl (B55), i-propyl (B36), benzyl (B17), p-nitro-benzyl (B45), p-methoxy-benzyl (B53), p-Cl-benzyl (B60), p-methyl-benzyl (B61), 3,4,5-trimethoxy-benzyl (B62);

C) derivatives of formula (I) having $R_3=H$, $R_1$ is benzyl, $R_2=CH_3CH_2$—CO— (B54), or $CH_3(CH_2)_5$—CO—(B46);

D) derivative of formula (I) in which $R_2=$—$COCH_3$, $R_3=R_1$ methyl (B42);

E) derivative of formula (I) having $R_2=$—$COCH_3$, $R_3=$methyl, $R_1=$isopropyl (B39), F) derivative of formula (I) in which $R_2=$benzoyl, $R_1=$benzyl, $R_3=H$ (B49), G) derivative of formula (I) wherein $R_2=$cyclopropylcarbonyl, $R_3=H$, and $R_1=$benzyl (B56).

The present invention further relates to therapeutical compositions, containing as the active ingredient one or more thiadiazole derivatives of general formula (I) wherein $R_1$ is selected from the class consisting of: $C_1$-$C_{10}$ linear or branched alkyl, benzyl, optionally substituted at the aromatic ring with one or more groups selected on their turn from the class consisting of: $C_1$-$C_{20}$ linear or branched alkyl residues , nitro groups, halogen atoms, $C_1$-$C_{20}$ linear or branched alkoxy, hydroxy and $C_2-C_{20}$ linear or branched acyloxy groups, $R_2$ is selected from H, $C_2-C_{10}$ alkanoyl, cycloalkanoyl wherein this ring has from 3 to 10 carbon atoms, aroyl, and $R_3$ is selected from H and $C_1-C_{10}$ alkyl, provided that when

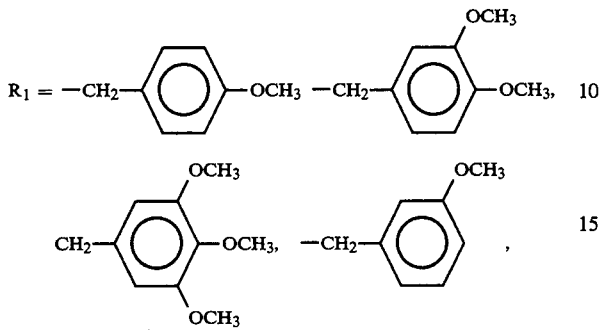

$R_2$ and $R_3$ must be different from H, in combination with suitable excipients and/or diluents.

In particular the therapeutical compositions of the present invention are suitable for the treatment of depressive states. The present invention further consists in the use of the thiadiazole derivatives of formula (I), wherein

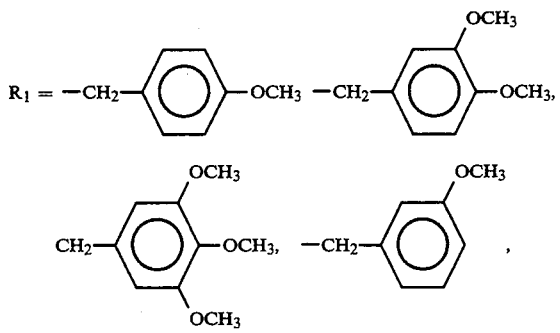

$R_2=R_3=H$, as the active ingredient for the preparation of therapeutical compositions to be used in human therapy for the treatment of depressive states and anxiety.

The present invention further relates to the process for preparing the thiadiazole derivatives of general formula (I), comprising one or more of the following steps:

a) reacting 5-mercapto-2-amino-1,3,4-thiadiazole of formula (II)

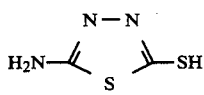

with an equimolar amount of the derivative of formula $R_1Cl$ wherein $R_1$ has the above mentioned meanings, in an aqueous environment at alkaline pH at 0° C., thereby obtaining the thiadiazole derivative of formula (I) wherein $R_1$ has the above mentioned meanings and $R_2=R_3=H$;

b) reacting the derivative obtained in step (a) with equimolar amounts of the compounds $R_2Cl$, wherein $R_2$ is selected from aroyl and cycloalkanoyl;

b') reacting the derivative of formula (I) coming from step (a) with equimolar amounts of the anhydride having formula $R(CO)_2O$, wherein R is a $C_1-C_9$ alkyl, in the solution of the corresponding acid RCOOH, thereby obtaining the derivative of formula (I) wherein $R_1$ has the above mentioned meanings and $R_2$ is a $C_2-C_{10}$ alkanoyl, $R_3=H$;

c) reacting the derivative of formula (I) coming from step (b) or (b') in a dipolar aprotic solvent, preferably dimethyl formamide in the presence of a halide acid acceptor with $R_3X$, wherein $R_3=C_1-C_{10}$ alkyl and X=halogen, thereby obtaining the derivative of formula (I) wherein $R_1$ and $R_2$ have the above mentioned meanings and $R_3$ is a $C_1-C_{10}$ alkyl.

The following examples of the present invention are reported for illustrative but not limitative purposes.

EXAMPLE 1

2-amino-5-benzylmercapto-1,3,4-thiadiazole (B16) synthesis (Step a)

13.31 g (0.1 mol.) 2-amino-5-mercaptothiadiazole (AMTD) are suspended in an amount of 0.5 moles water (about 9 cc), then 85% KOH is added in a sufficient amount to have an equimolar ratio KOH-AMTD (about 6.6 g). When the solution becomes fluid 12.66 g (0.1 moles) benzyl chloride are added and the mixture is stirred at 0° C. for 30'. The reaction progress is followed by TLC, by using as the eluant ether or a mixture of benzene and ethanol in a volumetric ratio 9:1. Afterwards an amount of water 5 times higher then that initially used (about 30 cc) is added and the mixture is left under rest for several hours. The formed precipitate is washed with water and ether, and crystallized from methanol. A white-cream powder is obtained, having a melting point: 158°-160° C.; the substance is soluble in alcohols, chloroform, ethyl acetate, acetone; insoluble in ether and water. The yield is about 50%.

The following derivatives of formula (I) are prepared analogously with similar yields, hereinbelow reported are also the corresponding melting points and the corresponding crystallization solvents:

| A) $R_1$ | $R_2 = R_3 = H$ Initials m.p. (°C.) | crystallization solvent |
|---|---|---|
| Methyl | B21 180 | ethyl acetate |
| ethyl | B34 137-138 | methanol |
| n-propyl | B32 117-119 | ethyl acetate |
| i-propyl | B35 150-151 | methylenchloride |
| p-nitrobenzyl | B43 171-172 | ethanol |
| p-methoxybenzyl | B51 151-153 | ethyl acetate |
| p-Cl-benzyl | B57 168-169 | ethyl acetate |
| p-methyl benzyl | B58 181-182 | ethanol |
| 3,4,5-trimethoxy-benzyl | B59 180-181 | ethanol |
| 3-methoxybenzyl | B63 148-149 | ethyl acetate |

EXAMPLE 1-A 2-amino-5-(3-acetoxy)-benzylmercapto-1,3,4-thiadiazole (B90/1) and 2-amino-5-(3-hydroxy)benzylthio-3,1,4 thiadiazole (B90/2) synthesis (step a)

Synthesis of 3-acetoxy-benzylalcohol (B88)

8.5 g 3-hydroxybenzyl-alcohol, are dissolved in 11 ml 5.45M KOH, while cooling the reaction mixture with ice. 6.5 ml acetic anhydride are then added in 15 minutes to the solution thus obtained.

An equal volume ethyl ether is added, and the organic phase is separated, washed with water, dried on anhydrous sodium sulfate and finally evaporated. The obtained product is then distilled (b.p. 120°-130° C.), then purified by silica gel chromatographic column (eluant cyclohexane/ethyl acetate 5.5: 4.5). A substantially pure product is obtained to be used for the successive reaction (yield 60%)

Synthesis of 3-acetoxybenzylchloride (B89)

The product coming from the preceding step is dissolved in benzene and a drop of pyridine is added. 2.45 ml thionyl chloride previously dissolved in benzene are then added to the obtained solution.

The mixture is left under stirring at room temperature for 4 hours, then concentrated under vacuum. The mixture is then dissolved in ethyl ether, the organic phase is then separated and washed with water, dried on anhydrous sodium sulfate, filtered and evaporated. The obtained product is then distilled (90°-95° C. 0.5 mm Hg), thereby obtaining a liquid which is then subjected to IR and NMR analyses (Field 65%).

Synthesis of 2-amino-5-(-3-acetoxy)benzylmercapto-1,3,4-thiadiazole (B90/1) and 2-amino-5-(3-hydroxy)-benzylthio-1, 3,4 thiadiazole (B90/2)

1.79 g 2-amino-5-mercapto-1,3,4-thiadiazole are suspended in 18 ml water. The mixture is cooled with ice, then 0.9 g 85% KOH are added and diluted with 35 ml ethanol.

3-acetoxybenzylchloride (2.5 g) is then dissolved in the reaction environment and the obtained mixture is maintained under stirring at 0° C. for 30', and at room temperature for about 5 hours.

A raw product is obtained which is filtered under vacuum and washed with water.

The filtered product is dried on air and crystallized by using ethyl acetate, thereby obtaining 2-amino-5-(-3-acetoxy)-benzylmercapto-1, 3,4-thiadiazole, characterized by having a melting point of 147°-148° C. (yield 47%).

The formed precipitate is then recovered from mother liquors by filtration under vacuum, washing with water and drying on air. The obtained product is then purified by treating it with chloroform at room temperature and filtering it under vacuum and by repeating the above operating conditions several times. The recovered product is treated with chloroform at the boiling temperature and filtered under vacuum, it is finally dried, thereby recovering the corresponding 3-hydroxy derivative, showing a melting point 176°-178° C. (yield 39%).

EXAMPLE 1-B

Synthesis of 2-amino-5-(4-acetoxy)-benzylmercapto-1,3,4-thiadiazole (B92/1) and 2-amino-5-(4-hydroxy)benzylthio-1,3,4 thiadiazole (B92/2)

Synthesis of 4-acetoxy-benzylalcohol (B87)

8.4 g 4-hydroxybenzyl-alcohol, are dissolved in 11 ml 5.45M KOH, while cooling the reaction mixture with ice. 6.48 ml acetic anhydride are then added in 15 minutes to the solution obtained. An equal volume of ethyl ether is added, and once the organic phase is separated, it is washed with a NaHCO$_3$ oversaturated solution and dried on anhydrous sodium sulphate and finally evaporated. The obtained product is then distilled (b.p. 140°-150° C.) under vacuum (3 mm Hg), then purified by silica gel chromatographic column (eluant cyclohexane/ethyl acetate 8: 2). A substantially pure product is obtained to be used for the successive reaction (yield 45%)

Synthesis of 4-acetoxybenzylchloride (B91)

The product (3 g) coming from the preceding step is dissolved in 7.5 ml benzene and a drop of pyridine is added. 2.17 ml thionyl chloride dissolved in benzene ape then added to the obtained solution.

The mixture is left to stir under reflux fop 1 hour, then it is concentrated under vacuum, dissolved in ethyl ether, the organic phase is separated and washed with water, dried on anhydrous sodium sulfate, filtered and evaporated (yield 50%).

Synthesis of 2-amino-5-(4-acetoxy)benzylmercapto-1,3,4-thiadiazole (B92/1) and 2-amino-5-(4-hydroxy)-benzylthio-1,3,4 thiadiazole (B92/2)

2 g 2-amino-5-mercapto-1,3,4-thiadiazole are suspended in 15 ml water. The mixture is cooled with ice, then 1 g 85% KOH are added and diluted with 40 ml ethanol.

4-acetoxybenzylchloride (2.78 g) is then dissolved in the reaction environment and the obtained mixture is maintained under stripping at 0° C. for 30', and at room temperature for about 5 hours. The reaction mixture is then concentrated under vacuum and maintained for 1 night at 0° C.

A raw product is obtained which is filtered under vacuum and washed with water.

4-acetoxy-derivative is obtained by treating the obtained precipitate with chloroform and successively filtering it under vacuum. The process is repeated several times and at the end the chloroform is evaporated, thereby recovering a raw product, which is then purified by chromatography on silica gel column, eluting the column with a mixture cyclohexane-ethyl acetate 3:7 (yield 40%).

The corresponding 4-hydroxy derivative is obtained from the residue of the preceding treatment with chloroform. The product is obtained by heating the same solvent to the boiling point and filtering under vacuum at the same temperature (28%).

EXAMPLE 1-C

Synthesis of 2-amino -5-(4-acetoxy-3-methoxy)-3-benzylthio-1,3,4-thiadiazole (B93).

Synthesis of 4-acetoxy-3-methoxy-benzylalcohol 2 g (3-methoxy-4-hydroxy) benzyl-alcohol (MW 154.17, 0.013 mol), are dissolved in 4 ml of 5.45M KOH aqueous solution, while cooling the reaction mixture with ice. As soon as this reactant results completely dissolved 1,3 g acetic anhydride (0.013 mol) are then added dropwise. The reaction is left under stirring for about three hours until completion for about three hours (TLC eluant: ethyl acetate/cyclohexane 6:4).

The reaction mixture is extracted with diethyl ether and the organic phase is washed carefully with water. The Organic phase is then dried on anhydrous sodium sulfate, filtered and evaporated to dryness. The oily raw product thus obtained results to be sufficiently pure from 1H-NMR analysis and it can be therefore used for the successive reaction (yield 78%).

$^1$H-NMR (CDCl$_3$) (CDCl$_3$) δ:2.3 (s,3H, OCOCH$_3$); 3.8 (s, 3H, OCH$_3$); 4.6 (d, J=4.3 Hz, 2H, CH$_2$); 4.8 (broad. s, exchanges with D$_2$O, 1H, OH); 6.9 (dd) J$_{ortho}$=8 Hz, J$_{meta}$=1 Hz, 1H, H$_6$); 7.0-7.1 (m, 2H arom, H$_2$+H$_5$. )

Synthesis of 4-acetoxy-3-methoxy-benzylchloride

The product (1.5 g) coming from the preceding step is dissolved in 4 ml benzene and a drop of pyridine is added. 1.5 ml thionyl chloride previously dissolved in 4 ml benzene are then added drop by drop to the obtained solution.

The mixture is left under stirring at room temperature for about three hours until the reactant disappears (TLC eluant : ethyl acetate/cyclohexane 6:4). The solvent is evaporated under reduced pressure and the residue is diluted with diethyl ether . The ethereal solution is repeatedly washed with water and dried on anhydrous sodium sulfate, filtered and evaporated under reduced pressure. The raw product thus obtained is distilled at 200° C. P=2 mm Hg), thereby recovering an uncoloured oil which slowly solidifies (yield 50%). $^1$H-NMR (CDCl$_3$) (CDCl$_3$) δ:2.3 (s,3H, OCOCH$_3$); 3.8 (s, 3H, OCH$_3$); 4.6 (s, 2H, CH$_2$); 6.95 (dd, J$_{ortho}$=8.2 Hz, J$_{meta}$=1.6 Hz, 1H, H$_6$); 7.0–7.1 (m, 2H arom, H$_2$+H$_5$.) Synthesis of 2-amino-5-(3-methoxy-4-acetoxy)benzylmercapto-1,3,4-thiadiazole (B93)

0.4 g 2-amino-5-thio-1,3,4-thiadiazole (MW 133, 0.003 mol) are suspended in 2 ml water. The mixture is cooled with ice, then 0.168 g KOH (pearls), and after some minutes a complete dissolution is observed. 4.5 cc ethanol are then added to the reaction mixture together with 0.53 g of 4-acetoxy-3-methoxybenzylchloride. After about 1 hour the precipitation of a white fine solid is observed. The reaction mixture is maintained under stirring for about 4 hours until its completion (TLC eluant: ethyl acetate/cyclohexane 6:4), then it is maintained at 0° C. for 12 hours. The formed solid is thus filtered and washed with ethanol, it is further crystallized from ethanol (yield 75%).

m.p. 139°–140° C. $^1$H-NMR (DMSO) δ:2.3 (s,3H, OCOCH$_3$); 3.7 (s, 3H, OCH$_3$); 4.3 (s, 2H, CH$_2$); 6.93 (dd, J$_{ortho}$=8.1 Hz, J$_{meta}$=1.9 Hz, 1H, H$_2$); 7.3 (broad s, exchanges with D$_2$O, 2H, NH$_2$).

EXAMPLE 2

2-acetylamino-5-benzylmercapto-1,3,4-thiadiazole (B17) synthesis (step b').

5 g (0.022 mol) B16 are suspended in 2.28 ml (0.024 mol) acetic anhydride then 9 cc glacial acetic acid are added. The mixture is heated to 35°–40° C. until it becomes clear, (the reaction progress is followed by TLC by using as the eluant benzene:ethanol=9:1) afterwards the mixture is left to cool as long as the first crystal appears. 11 cc water are added: a white precipitate forms which is removed by filtration. M.P.=170° C.

The following derivatives of formula (I) are prepared analogously; hereinbelow reported are the corresponding melting points and the corresponding crystallization solvents:

| A) R$_1$ | R$_3$ = H R$_2$ = —COCH$_3$ Initials m.p. (°C.) | crystallization solvent |
| --- | --- | --- |
| Methyl | B37 215–216 | ethanol |
| n-propyl | B55 135–136 | chloroform |
| i-propyl | B36 187–189 | acetone + ethanol |
| p-nitrobenzyl | B45 263–265 | ethanol |
| p-methoxybenzyl | B53 177–179 | ethanol |
| p-Cl-benzyl | B60 213–215 | ethanol |
| p-methyl benzyl | B61 212–213 | ethanol |
| 3,4,5-trimethoxy-benzyl | B62 200–201 | ethanol |

2-propionylamino-5-benzylmercapto-1,3,4-thiadiazole (B54), melting point (162°–163° C.) is prepared analogously to what previously described in example 2 starting from B16, propionic anhydride and also 2-hepthanoylamino-5-benzylmercapto-1,3,4-thiadiazole (melting point 123°–124 ° C.) is obtained, starting from B16 and heptanoic anhydride.

EXAMPLE 3

2-N-benzoylamino-5-benzylmercapto-1,3,4-thiadiazole (B49) synthesis (step b).

26.62 g (0.2 mol) 2-amino -benzylmercapto -1,3,4-thiadiazole (B16) prepared as in example 1 (step a), are dissolved in about 25 ml distilled water. When the mixture is clear, 25.32 g (0.2 moles) benzoyl chloride ape added and the mixture is stirred at 0° C. for 30 minutes. Afterwards 125 ml water are added and the mixture is left under rest for several hours. A white precipitate forms, which is filtered washed with water and ether and crystallized from ethanol. Melting point: 193°–194° C.

2-cyclopropylcarbonylamino-5-benzylmercapto-1,3,4 thiadiazole (B56) is prepared in an analogous way starting from the product B16 and cyclopropylcarbonyl chloride. Melting point 182°–184° C.

EXAMPLE 4

2-(N-methyl-N-acethyl)-amino-5-isopropylmercapto-1,3,4-thiadiazole (B39) synthesis (step c).

43.4 g (0.2) moles 2-N-acethyl-5-isopropylmercapto-1,3,4thiadiazole (B36) ape dissolved in 50 cc dimethylformamide. Then 1 g potassium carbonate and 28.4 g (0.2 moles) of methyl iodide are slowly added to the reaction mixture maintained under stirring . The same mixture is then left to react at low temperature (0° C.) for 30 minutes and 150 ml water are added; the mixture is left under rest fop some hours. A white precipitate forms that is filtered, washed with water and ether and crystallized from ethanol, (melting point 44°–45° C).

2-N-methyl-N-acetyl-5-methylmercapto-1,3,4-thiadiazole (B42) (melting point 72°–74° C.) is obtained in an analogous way starting from 2-N-acethyl-5-methylmercapto-1,3,4-thiadiazole (B37).

DISPAIR TEST

This behaviouristic test conceived by Porsolt (1977 —Nature, 266 730–732 is generally utilized to evaluate the antidepressant activity.

It is a very simple test to carry out , requiring a minimum equipping and having excellent predictive characteristics: as a matter of fact antidepressants of the three main classes: tricyclic, monoamine oxidase inhibitor and atypical antidepressants resulted positive to DISPAIR TEST.

Moreover a significant correlation between the clinical activity and the activity in the behaviouristic test was demonstrated (Porsolt 1977).

Another positive factor comes from the phenomenological analogy between the immobility shown by the animal, that is judged as a measure of its depressive state and what happens in a large number of depressive form in man, particularly in the mono and bipolar endogenous depression.

The animal behaviour does not represent a generalized hypoactivity but rather an incapacity to maintain the effort to try to escape. In agreement with this behaviouristic aspect the depressed subjects demonstrated pronounced psychomotor difficulties in those tests requiring a sustained effort. (Weingartner and Silberman 1982 Psychoph. Bull. 18: 27–42).

METHOD

Swiss strain male mice of average weight of 30 g (CD-1 Charles River) casually assigned to the different treatment groups are used.

The method consists in placing the animal in a plexiglas cylinder 25 cm high and with a diameter of 9 cm filled with water at 24° C. up to a level of 6 cm.

The test lasts 6 minutes and the time in which the animal lets itself float without reacting is measured starting from the $2^{nd}$ minute (immobility duration).

The animals ape treated by intraperitoneal route (injection volume 10 ml/kg) 1 hour before the test.

The evaluation is carried out in blind. The statistical analysis of the results is carried out where it is possible by means of the T-Student test, otherwise the non parametric test of Mann Whitney is used.

The results of the Dispair Test ape reported in the following table:

TABLE 1

Dispair Test results in mice:

| compound | dosage (mg/kg) | immobility duration | < % | p |
|---|---|---|---|---|
| B21 | 0 | 209 ± 15 | | |
| | 20 | 187 ± 13 | 8 | 0.05 |
| | 25 | 175 ± 31 | 16 | 0.05 |
| | 50 | 161 ± 26 | 23 | 0.016 |
| | 60 | 176 ± 21 | 16 | 0.008 |
| | 75 | 170 ± 39 | 19 | 0.05 |
| | 100 | 187 ± 25 | 11 | N.S. |
| B35 | 0 | 199 ± 17 | | |
| | 10 | 165 ± 42 | 17 | 0.05 |
| | 15 | 194 ± 14 | | N.S. |
| | 20 | 185 ± 11 | | N.S. |
| B36 | 0 | 196 ± 18 | | |
| | 0.5 | 178 ± 33 | | N.S. |
| | 1 | 159 ± 23 | 19 | 0.002 |
| | 2.5 | 188 ± 16 | | N.S. |
| | 5 | 196 ± 22 | | N.S. |
| | 12.5 | 199 ± 15 | | N.S. |
| B39 | 0 | 188 ± 23 | | |
| | 0.125 | 180 ± 19 | | N.S. |
| | 0.25 | 155 ± 36 | 18 | 0.01 |
| | 0.5 | 169 ± 30 | 10 | 0.02 |
| | 1 | 161 ± 14 | 14 | 0.01 |
| | 5 | 176 ± 28 | | N.S. |
| | 10 | 204 ± 18 | | N.S. |
| B16 | 0 | 203 ± 8 | | |
| | 1 | 197 ± 22 | | N.S. |
| | 5 | 171 ± 23 | 16 | 0.02 |
| | 10 | 132 ± 45 | 35 | 0.002 |
| | 15 | 186 ± 14 | 8 | 0.02 |
| | 20 | 199 ± 16 | | N.S. |
| B51 | 0 | 188 ± 19 | | |
| | 0.01 | 200 ± 19 | | N.S. |
| | 0.03 | 164 ± 29 | 13 | 0.009 |
| | 0.1 | 166 ± 13 | 12 | N.S. |
| | 0.3 | 158 ± 24 | 16 | 0.0007 |
| | 1.25 | 174 ± 40 | | N.S. |
| | 5 | 189 ± 15 | | N.S. |
| B17 | 0 | 204 ± 15 | | |
| | 0.03 | 198 ± 16 | | N.S. |
| | 0.06 | 159 ± 38 | 22 | 0.05 |
| | 0.125 | 167 ± 22 | 17 | 0.002 |
| | 0.25 | 183 ± 20 | 10 | 0.05 |
| | 0.5 | 182 ± 25 | 10 | N.S. |
| | 1 | 187 ± 36 | | N.S. |
| B45 | 0 | 195 ± 9 | | |
| | 0.1 | 182 ± 22 | | N.S. |
| | 0.25 | 167 ± 26 | 16 | 0.02 |
| | 0.5 | 166 ± 18 | 16 | 0.002 |
| | 1 | 183 ± 17 | | N.S. |
| B53 | 0 | 182 ± 16 | | |
| | 0.1 | 182 ± 16 | | N.S. |
| | 0.5 | 165 ± 25 | 10 | 0.05 |
| | 1 | 151 ± 29 | 15 | 0.05 |
| | 2 | 195 ± 31 | | N.S. |
| B63 | 0 | 202 ± 21 | | |
| | 0.05 | 187 ± 34 | | N.S. |
| | 0.1 | 171 ± 26 | 15 | $4 \times 10^{-3}$ |
| | 0.25 | 159 ± 22 | 21 | $3 \times 10^{-4}$ |
| | 0.5 | 166 ± 25 | 18 | $2 \times 10^{-3}$ |
| | 1.0 | 174 ± 30 | 14 | $2 \times 10^{-2}$ |
| | 10 | 187 ± 26 | | |

As it can be deduced from the above reported data, these compounds are active at low dosage (10 mg/kg for B35, 5–10 mg/kg for B16, 1 mg/kg for B36, about 0.50 mg/kg for B51 and B17). Imipramine is active at dosage of 20 mg/kg in the same tests; therefore the compounds according to the present invention are generally more effective than said known comparison antidepressant.

ACUTE TOXICITY

The LD50, evaluated on mice of some compounds of the present invention is reported hereinbelow:

| Compound | DL50 |
|---|---|
| B17 | >1 g/kg both per os and i.p. |
| B21 | >1 g/kg i.p. |
| B16 | >600 mg/kg both i.p. and per os. |

ANXIOLYTHIC ACTIVITY TEST

The behaviouristic Social Interaction test found by FILE was used. (Animal models of psychiatric disorders, vol. 1 Karger, Basel, pp 151-166).

It consists in an experimental procedure permitting to evaluate the influence of the pharmacological treatment on the spontaneous behaviour of the rat, by means of the social component which in this animal is particularly accentuated.

In fact it has been demonstrated that fats exposed to anxiogen conditions such as unfamiliar environment and considerable lighting, exhibit a social interaction reduction and this reduction is countered by conventional benzodiazepine type and new generation anxiolythic drugs, acting on various serotonine receptors types (5-HT1A agonists; 5-HT2 and 5-HT3 antagonists)

METHOD

Sprague-Dawley male rats weighing about 250 g are used. After a normal stabling period (2 weeks), the animal are isolated in smaller cages ($267 \times 207 \times 140$ mm surface 410 cm$^2$) for a period of about 5 days.

Then the rats are gathered into couples, avoiding that weight difference between the two animals overcomes 10 g and that the couple components had not previously stabled together.

The couple thus gathered are assigned to the respective treatment group.

Diazepam was utilized as the positive control drug: 1,25 mg/kg are intraperitoneally administered 30' before carrying out the test.

The compounds to be tested are administered 1 hour before carrying out the test.

Diazepam increases Social Interaction if compared to the controls of an amount comprised between about 70 and 100%.

The box utilized [55×55×30 cm (height)] for the animal observation is white, completely washable and provided with a floor split up into 25 squares.

A 100 Watt lamp is placed upon the box at 50 cm from the floor. The test is realized in a remote room whose only light source is represented by the lamp lighting the box.

The evaluation is carried out in blind. The animals are observed indirectly, by means of a mirror suitably placed.

TEST DURATION

Evaluated parameters: time passed in Social Interaction (sniffing pursuit, grooming, boxing etc.).

The box is systematically cleaned up after every test.

EFFECTS OF B16 AND B63 ON RAT SOCIAL INTERACTION AND BRIEF DESCRIPTION OF THE DRAWINGS

The results are expressed as a function of a percentage increase of Social Interaction of the treated animals in comparison with the controls.

Figure 2:
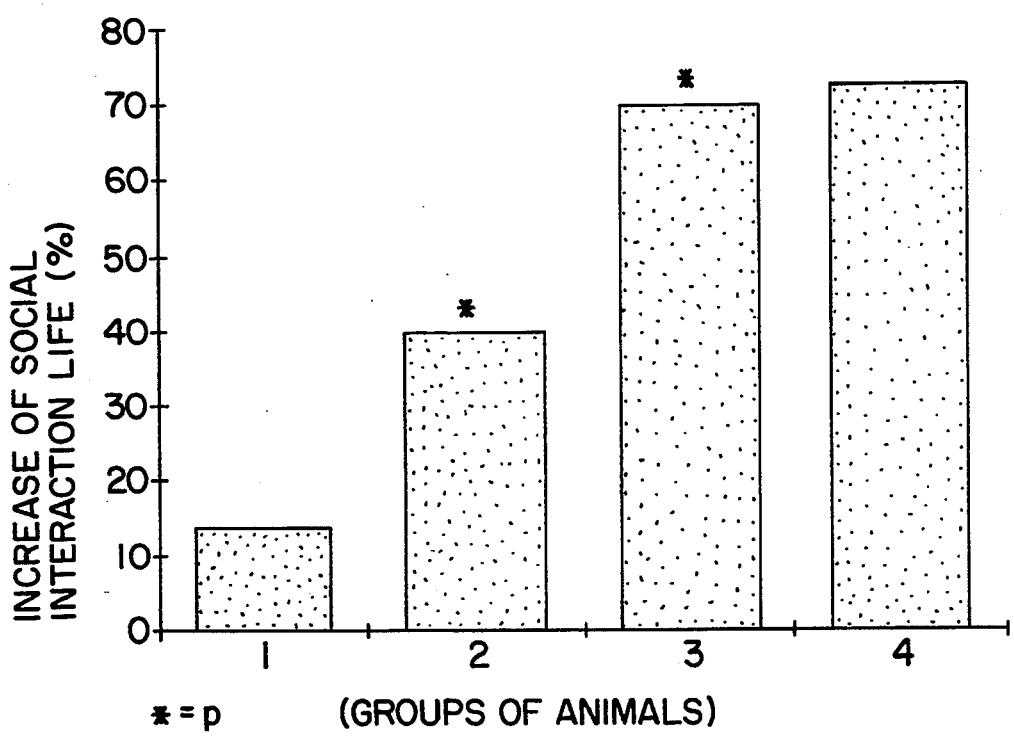

The data relative to B16 are reported in FIG. 1 and in Table 2 The dose-response curve has a Gaussian shape. The data relative to B63 are reported in FIG. 2 Table 3.

TABLE 2

| GROUP | administered dose (mg/kg) | (B16) Social Interaction increase (%) | p |
|---|---|---|---|
| 1) | (n = 6) 0.5 | 40 | 0.2 N.S. |
| 2) | (n = 4) 1 | 67 | $3 \times 10^{-2}$ |
| 3) | (n = 5) 2.5 | 94 | $2 \times 10^{-2}$ |
| 4) | (n = 6) 5 | 51 | 0.1 N.S. |

TABLE 3

| GROUP | administered dose (mg/kg) | (B63) Social Interaction increase (%) | p |
|---|---|---|---|
| 1) | 0.25 | 14 | N.S. |
| 2) | 0.5 | 40 | 0.02 |
| 3) | 1 | 70 | 0.01 |
| 4) | 2.5 | 73 | 0.06 N.S. |

We claim:

1. A therapeutical method for the treatment of depressive states and anxiety, comprising administering an effective amount of a thiadiazole derivative of general formula (I)

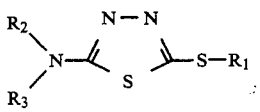
(I)

wherein $R_1$ is selected from the group consisting of $C_1$–$C_{10}$ linear or branched alkyl, benzyl, benzyl which is substituted on the aromatic ring with one or more groups selected from the group consisting of $C_1$–$C_{20}$ linear or branched alkyl groups, nitro groups, halogen atoms, $C_1$–$C_{20}$ linear or branched alkoxy groups, hydroxy and $C_2$–$C_{10}$ linear or branched acyloxy groups, $R_2$ is selected from the group consisting of H, $C_2$–$C_{20}$ alkanoyl, cycloalkanoyl wherein the ring has from 3 to 10 carbon atoms, aroyl and $R_3$ is selected from the group consisting of H and $C_1$–$C_{10}$ alkyl.

2. A method as defined in claim 1 wherein the thiadiazole derivative is administered in combination with a suitable diluent and/or excipient.

3. A therapeutic method for the treatment of depressive states and anxiety comprising administering an affective amount of thiadiazole derivative of formula (I)

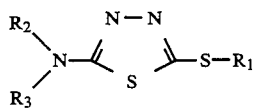

wherein:

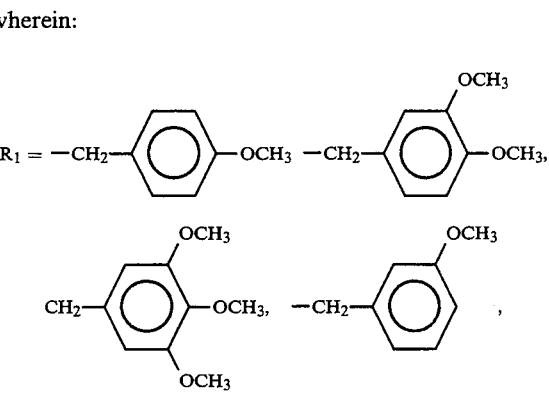

$R_2 = R_3 = H$.

4. A therapeutical method according to claim 1 wherein the thiadiazole derivative is selected from the group consisting of:
2-amino-5-benzyl-mercapto-1,3,4-thiadiazole;
2-amino-5-methyl-mercapto-1,3,4-thiadiazole;
2-amino-5-iso-propyl-mercapto-1,3,4-thiadiazole;
2-amino-5-(p-methoxy)-benzyl-mercapto-1,3,4-thiadiazole;
2-amino-5-(3-methoxy)-benzyl-mercapto-1,3,4-thiadiazole;
2-acetylamino-5-iso-propyl-mercapto-1,3,4-thiadiazole;
2-acetylamino-5-(p-nitro)-benzyl-mercapto-1,3,4-thiadiazole; 2-acetylamino-5-(p-methoxy)-benzyl-mercapto-1,4-thiadiazole and 2-(N-methyl)acetylamino-5-iso-propylmercapto-1,3,4-thiadiazole.

* * * * *